United States Patent

Weaver et al.

[11] Patent Number: 5,955,564
[45] Date of Patent: Sep. 21, 1999

[54] 1,5(8)-BIS (SUBSTITUTED-N-PROPYLAMINO)-4,8(5)-BIS(ARYLTHIO) ANTHRAQUINONE COMPOUNDS

[75] Inventors: Max Allen Weaver; James John Krutak, Sr., both of Kingsport; Clarence Alvin Coates, Jr., Blountville, all of Tenn.

[73] Assignee: Eastman Chemical Company, Kingsport, Tenn.

[21] Appl. No.: 08/975,738

[22] Filed: Nov. 21, 1997

Related U.S. Application Data

[60] Provisional application No. 60/032,361, Nov. 27, 1996.
[51] Int. Cl.$^6$ ............... C08G 4/00; C08G 10/00; C08G 14/00
[52] U.S. Cl. ........... 528/223; 528/224; 528/226; 528/228; 528/125; 528/127; 528/128; 528/272
[58] Field of Search ................... 528/223, 224, 528/226, 228, 125, 127, 128, 272

[56] References Cited

U.S. PATENT DOCUMENTS

| | | |
|---|---|---|
| 4,804,719 | 2/1989 | Weaver et al. . |
| 4,841,057 | 6/1989 | Miura et al. . |
| 4,999,418 | 3/1991 | Krutak et al. . |

FOREIGN PATENT DOCUMENTS

| | | |
|---|---|---|
| 0 040 139 A2 | 11/1981 | European Pat. Off. . |
| 0 275 077 A1 | 1/1988 | European Pat. Off. . |
| 0 415 859 A1 | 3/1991 | European Pat. Off. . |

*Primary Examiner*—Duc Truong
*Attorney, Agent, or Firm*—Jonathan D. Wood; Karen A. Harding; Harry J. Gwinnell

[57] ABSTRACT

This invention relates to new blue anthraquinone colorants having Formula I

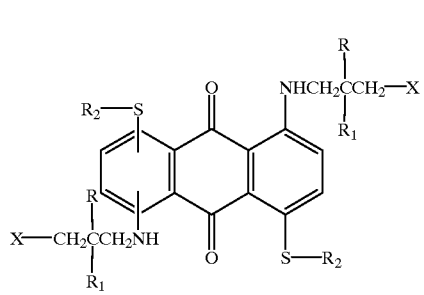

wherein R and R1 are the same or different and are selected from hydrogen and unsubstituted or substituted C1–C6 alkyl, C3–C7 cycloalkyl 2-furyl, 2-thienyl, or phenyl; R2 is aryl; X is a group selected from hydroxy, C1–C6 alkanolyloxy, carboxy, C1–C6 carbalkoxy and carbamoyloxy.

The colorants are useful for copolymerizing into polymers such as polyesters and polyurethanes. In particular, they are advantageous for preparing colored sulfopolyesters which are useful for coloring human hair.

7 Claims, No Drawings

1,5(8)-BIS (SUBSTITUTED-N-PROPYLAMINO)-4,8(5)-BIS(ARYLTHIO) ANTHRAQUINONE COMPOUNDS

RELATED APPLICATION

This application is based upon and claims the priority of provisional application 60/032,361 filed Nov. 27, 1996.

BACKGROUND OF THE INVENTION

Various compounds have been disclosed for coloring hair. For example, U.S. Ser. No. 08/476,303 discloses several useful colorants. Example 13 describes the preparation of a polymer containing a difunctional blue anthraquinone colorant and Example 14 describes dispersing the blue polymer in hot water. It has been found that the dispersion of Example 14 is not stable and sludging results and the polymer is extremely difficult to disperse in contrast to the sulfo-polyesters prepared from the dyes of the present invention.

U.S. Pat. No. 4,999,418 discloses anthraquinone compounds having the formula $AQ[NHCH_2C(R_1)R_2CH_2X]_n$ wherein AQ is the residue of a 9,10-anthraquinone radical; $R_1$ and $R_2$ are the same or different and are unsubstituted alkyl, cycloalkyl or aryl; X is a group reactive with at least one monomer from which polyester is prepared; n is 1 or 2. Column 2 (lines 35–38) provides the list of possible substituents on the anthraquinone ring. Included in this list of substituents is arylthio; however, diarylthio substituted anthraquinone compounds similar to those of the present invention are not disclosed. The compounds of Examples 61 and 86 contain only one arylthio group and the compound of Example 62 contains two methythio groups. Neither of these colorants has a desirable shade of blue and the colorant of Example 86 would be difficult to prepare on a commercial scale since in involves the use of the very volatile and odoriferous methylmercaptan.

U.S. Pat. No. 4,804,719 describes a variety of colorants which are useful for copolymerizing to prepare water-dissipatable polyester and polyester-amides containing a variety of copolymerized colorants. There is no disclosure of the anthraquinone compounds of the present invention, however.

U.S. Pat. No. 4,841,057 discloses 1,5-diamino-4,8-diarylthioanthraquinones. These colorants are not thermally stable when added to a polyester forming reaction and drastic color changes are observed in contrast to the colorants of this invention.

DESCRIPTION OF THE PRESENT INVENTION

The present invention relates to novel anthraquinone blue colorant compositions corresponding to Formula I

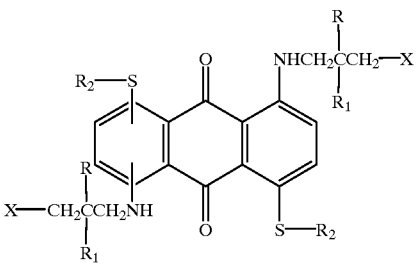

wherein R and R1 are the same or different and are selected from hydrogen and unsubstituted or substituted $C_1$–$C_6$ alkyl, $C_3$–$C_7$ cycloalkyl, 2-furyl, 2-thienyl, or phenyl; $R_2$ is aryl; X is a reactive group selected from hydroxy, $C_1$–$C_6$ alkanoyloxy, carboxy, $C_1$–$C_6$ carbalkoxy and carbamoyloxy and are particularly useful for producing blue sulfo-containing, water dispersible polymeric compositions which are useful for coloring human hair. The polymers containing the copolymerized residues of colorants of Formula I are particularly easy to disperse in hot water and the dispersion is stable on storage without any residue or sludge being formed.

The compounds of the present invention are thermally stable, readily prepared from available intermediates and useful in copolymerizing into sulfo-containing, linear, water-dispersible polyesters and/or polyester amides to prepare polymeric colorants.

The compounds of the present invention are also useful when dispersed with typical ionic dispersants, such as sodium lignin sulfonates, as disperse dyes for dyeing textile fibers such as cellulose acetate, polyamides and polyesters. Also, they may be used for coloring a variety of thermoplastics by solvent blending or melt blending followed by extrusion into films, fibers, etc.

The compounds are useful for copolymerizing into polymers such as, but not limited to, polyesters and polyurethanes. In particular, they are advantageous for preparing colored sulfopolyesters which are useful for coloring human hair.

The compounds of Formula I are prepared by reacting 1,5(8) dichloroanthraquinone with the appropriate amines II to give the red intermediates III:

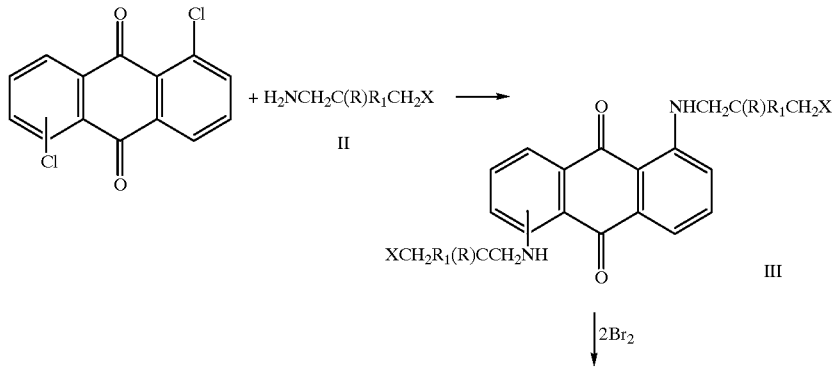

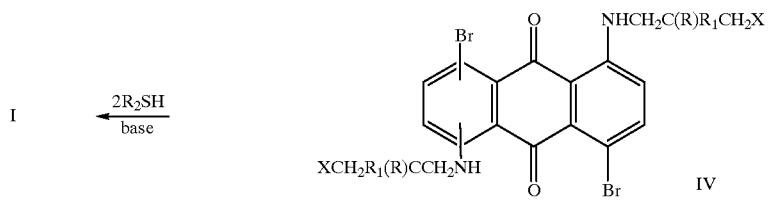

The conditions for preparing III are well described in U.S. Pat. No. 4,999,418, except where R and $R_1$ are both hydrogen. These compounds are prepared similarly using 3-aminopropanol. Compounds III are then dibrominated using bromine in solvents such as pyridine, picolines, acetic acid, propionic acid, etc. or by using brominating agents such as N-bromosuccinimide and 1,3-dibromo-5,5-dimethylhydantoin in an aprotic solvent such as N,N-dimethylformamide to produce dibromominated compounds IV. Blue colorants of Formula I are then conveniently prepared by reacting compounds of Formula IV with at least two equivalents of an arylmercaptan ($R_2SH$) in the presence of bases such as alkali metal carbonates, alkali metal bicarbonates, tertiary amines, etc. in aprotic solvents such as N,N-dimethylformamide, N,N-dimethylacetamide or N-methyl-2-pyrrolidonone or in higher boiling alcohols, particularly $C_1$–$C_4$ alkoxyethanols. The reaction may be facilitated by the presence of copper or copper salts.

In the description of the compounds of Formula I above, the terms "$C_1$–$C_6$ alkyl" and "substituted $C_1$–$C_6$ alkyl" are used to describe straight or branched chain alkyl groups containing 1 to 6 carbon atoms and these groups substituted with one or more groups selected from halogen, $C_1$–$C_6$ alkoxy, $C_3$–$C_8$ cycloalkyl, phenyl and cyano, respectively.

The terms "$C_3$–$C_8$ cycloalkyl" and "substituted $C_3$–$C_8$ cycloalkyl" are used to described cycloaliphatic hydrocarbon radicals containing 3 to 8 carbons and these substituted with at least one $C_1$–$C_6$ alkyl group, respectively.

The term "substituted phenyl" is used to describe the phenyl radical containing at least one substituent selected from $C_1$–$C_6$ alkyl, $C_1$–$C_6$ alkoxy and halogen.

The term aryl is used to describe phenyl and naphthyl and these radicals substituted with one or more groups selected from $C_1$–$C_6$ alkyl, $C_1$–$C_6$ alkoxy, hydroxy, cyano, halogen, phenyl, cyclohexyl, trifluoromethyl, $C_1$–$C_6$ alkylsulfonyl, phenoxy, phenylthio, sulfamoyl and carbamoyl.

The term halogen is used to refer to fluorine, chlorine, bromine and iodine.

In the above definitions, the terms "$C_1$–$C_6$ alkoxyl", "$C_1$–$C_6$ alkylsulfonyl", "$C_1$–$C_6$ alkanoyloxy" and "$C_1$–$C_6$ carbalkoxy" are used to describe groups wherein the alkyl portion thereof contains 1 to 6 carbon atoms and which may be substituted as described above.

The terms "sulfamoyl" and "carbamoyl" are used to describe the radicals —$CON(R_3)R_4$ and —$SO_2N(R_3)R_4$ respectively, wherein $R_3$ and $R_4$ are independently selected from hydrogen; $C_1$–$C_6$ alkyl; $C_3$–$C_8$ cycloalkyl; phenyl and phenyl substituted with at least one group selected from $C_1$–$C_6$ alkyl, $C_1$–$C_6$ alkoxy and halogen.

The term "carbamoyloxy" is used to describe the radical —$OCON(R_3)R_4$, wherein $R_3$ and $R_4$ are as defined previously.

In a preferred embodiment of the invention, the colorants correspond to structure I wherein R and $R_1$ are hydrogen and/or methyl; X is selected from hydroxy and acetoxy; $R_2$ is selected from phenyl and phenyl substituted with methyl, ethyl, t-butyl, cyclohexyl, hydroxy, halogen, methoxy and ethoxy or a combination of these.

The present invention further comprises water dissipatible polyester and polyester amide compositions containing the compositions of the present invention copolymerized therein. Thus, also disclosed herein are composition of matter comprising water-dispersible polymeric material having linking groups comprising at least about 20 mole % carbonyloxy and up to about 80 mole % carbonylamido, said material containing water-solubilizing sulfonate groups and having copolymerized onto or into the polymer backbone from about 0.01 to about 40 mole % based on the total of all reactant hydroxy, carboxy or amino equivalents, or the condensable derivative equivalents thereof, of colorant composition according to the present invention.

Preferably the polymer of the water dissipatible polymer has an inherent viscosity of from about 0.1 to about 1.0 measured in a 60/40 parts by weight solution of phenol/tetrachloroethane at 25° C. and at a concentration of 0.25 gram of polymer in 100 mL of the solvent, the polymer containing substantially equimolar proportions of equivalents (100 mole percent) to hydroxy and amino equivalents (100 mole percent), the polymer comprising the reaction residues of the following reactants (a), (b), (c), (d), and (e) or the ester forming or esteramide forming derivatives thereof:

(a) at least one difunctional dicarboxylic acid;

(b) from about 4 to about 25 mole percent, based on a total of all acid, hydroxyl and amino equivalents being equal to 200 mole percent, of at least one difunctional sulfomonomer containing at least one cationic sulfonate group attached to an aromatic or cycloaliphatic nucleus wherein the functional groups are hydroxy, carboxyl or amino;

(c) at least one difunctional reactant selected from a glycol or a mixture of a glycol and diamine having two —NRH groups, the glycol containing two —$CH_2$—OH groups of which (1) at least about 10 mole percent, based on the total mole percent of hydroxy or hydroxy and amino equivalents, is a poly(ethylene glycol) having the structural formula:

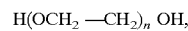

n being an integer of from 2 to 20, or (2) of which from about 0.1 to less than about 15 mole percent, based on the total mole percent of hydroxy or hydroxy and amino equivalents, is a poly(ethylene glycol) having the structural formula:

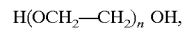

n being an integer of between 2 and 500, and with the proviso that the mole percent of said poly(ethlene glycol) within said range is inversely proportional to the quantity of n with said range;

(d) from none to at least one difunctional reactant selected from a hydroxycarboxylic acid having one —C(R)$_2$—OH group, an amino-carboxylic acid having one —NRH group, and an amino-alcohol having one —C(R)$_2$—OH group and one —NRH group, or mixtures of said difunctional reactants;

wherein each R in the (c) or (d) reactants is a H atom or an alkyl group of 1 to 4 carbon atoms; and (e) from about 0.1 mole % to about 15 mole %, based on a total of all acid, hydroxyl and amino equivalents being equal to 200 mole % of colorant composition according to claim 1.

Preferably the polymeric material contains less than about 10 mol %, based on all reactants, of reactant (d), at least about 70 mol % of reactant (c) is glycol, and at least about 70 mol % of all hydroxy equivalents is present in the glycol.

The following examples and Table I provide a more complete description of the practice and scope of the invention.

Suitable polymeric materials are more fully described in U.S. Pat. No. 4,804,719, which is incorporated herein by reference.

EXAMPLE 1

A mixture of 1,5-bis-[(3-hydroxy-2,2-dimethylpropyl) amino]anthraquinone (102.5g, 0.25 mole), acetic acid (2.5L) and acetic anhydride (102.1g, 1.00 mole was stirred and heated at 100° C. for 2 hrs. Thin layer chromatography (TLC) (50/50 cyclohexane/tetrahydrofuran) showed mostly complete acetylation, but some mono reacted product. Additional acetic anhydride (10.2g, 0.10 mole) was added and the reaction mixture was stirred 12 hrs. longer at 100° C. TLC showed essentially complete reaction. The mixture was allowed to cool somewhat and the product precipitated by the dropwise addition of water (1.5L) with stirring. The red 1,5-bis[(3-acetoxy-2,2-dimethylpropyl) amino] anthraquinone was collected by filtration, washed well with hot water and then dried in air (yield-114.9g). Field desorption mass spectrometry (FDMS) confirmed the structure.

EXAMPLE 2

A portion of the product of Example 1 (24.7g, 0.05 mole) and pyridine (300 mL) were mixed and heated to about 55° C. with stirring. Bromine (20.0g, 0.125 mole) was added dropwise over 0.5 hr. The mixture was then heated at 45–65° C. for about 6.0 hrs. Water (250 mL) was added dropwise to precipitate the brominated product, which was collected by filtration, washed with water, 50/50 water/methanol and hexane and dried in air (yield-30.1g). FDMS confirmed the product to be the desired 1,5-bis[(acetoxy-2,2-dimethylpropyl)amino]-4,8-dibromoanthraquinone.

EXAMPLE 3

A portion (16.25 g, 0.025 mole) of the dibrominated anthraquinone intermediate of Example 2, p-thiocresol (6.80g, 0.055 mole), potassium carbonate (8.30 g, 0.06 mole) and N,N-dimethylformamide (DMF) (250 mL) were mixed and heated at about 95° C. for 3.0 hrs. The reaction mixture was allowed to cool and ethanol (250 mL) was added. The blue product was collected by filtration and reslurried in hot methanol (100 mL). The cooled mixture was filtered and the blue product which was collected was washed with methanol and dried in air (yield-13.5 g). FDMS supported the following structure:

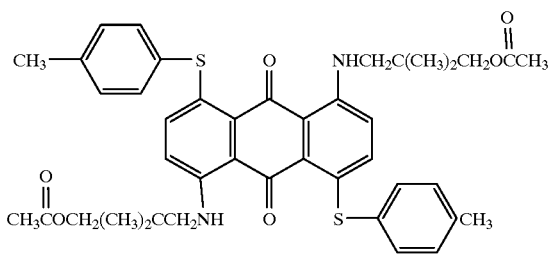

EXAMPLE 4

A mixture of 1,5-bis[(3-acetoxy propyl) amino] anthraquinone (21.9 g, 0.05 mole) and pyridine (250 mL) was heated with stirring to 35° C. Bromine (20.0g, 0.125 mole) was added dropwise at 35–40° C. to the solution and heating and stirring were continued at 35–45° C. for 3 hrs. Water (1.5L) was added dropwise with stirring. The precipitated product, 1,5-bis[(3-acetoxypropyl)amino]-4,8-dibromo-anthraquinone, was collected by filtration washed with water and dried in air (yield-27.7g) FDMS supported the proposed structure.

EXAMPLE 5

A portion (17.82 g, 0.03 mole) of the dibrominated anthraquinone intermediate of Example 4, p-thiocresol (7.7 g, 0.062 mole), potassium carbonate (8.3 g, 0.06 mole) and DMF (250 mL) were mixed and heated at about 95° C. for 4 hrs. The reaction mixture was drowned into water (750 mL) with stirring and the precipitated blue product was collected by filtration, washed with water and air dried (yield −19.0 g). FDMS supported the following desired structure:

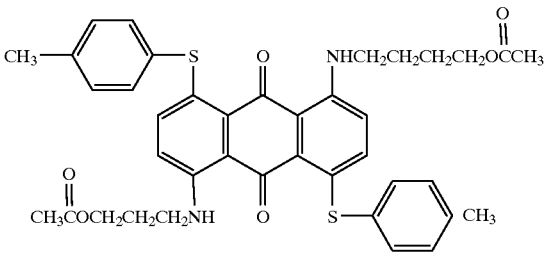

EXAMPLE 6

A mixture of 1,5-bis[(3-hydroxypropyl) amino] anthraquinone (35.44 g, 0.10 mole) and N,N-dimethylformamide (500 mL) was heated and stirred to 55° C. and then a solution of N-bromosuccinimide (35.61 g, 0.20 mole) dissolved in DMF (100 mL) was added dropwise over 0.5 hr., allowing the temperature to rise to about 60° C. Stirring and slight heating were continued and the temperature was maintained at about 55° C. for 2.0 hrs. The reaction mixture was allowed to cool to about 35° C. and water (500 mL) was added dropwise with stirring. The precipitated product was collected by filtration washed with water and dried in air (yield - 46.7 g). FDMS confirmed the product to be the desired 1,5-bis[(3-hydroxypropyl)amino]-4,8-dibromo-anthraquinone.

EXAMPLE 7

The dibrominated anthraquinone intermediate from Example 6 (46.0 g, 0.090 m), p-thiocresol (24.8g, 0.20 m), potassium carbonate (25.0 g, 0.18 m) and DMF (1.0L) were mixed and heated with stirring at about 95° C. for 3.0 hrs. Heat was removed and water (750 mL) was added dropwise with stirring. The solid product was collected by filtration, washed with hot water (3L) and dried in air. After being reslurried in methanol (600 mL) the product was again collected by filtration, washed with 50/50 water/methanol and dried in air (yield 47.3 g). FDMS supported the following structure:

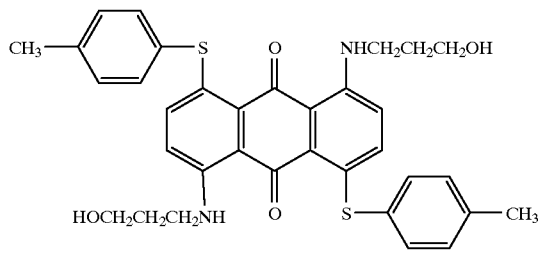

EXAMPLE 8

Components (a)–(f) comprising:
(a) 123.66 g (0.64m) dimethyl isophthalate
(b) 21.11 g (0.07 m) dimethyl 5-sodiosulfoisophthalate
(c) 119.22 g (1.12 m) diethylene glycol
(d) 0.75 g (0.0091 m) anhydrous sodium acetate
(e) 75 ppm Ti catalyst as titanium tetraisopropoxide (f) 20.0 g (0.027 m) blue colorant of Example 3 were added to a 500 mL round bottom flask that was fitted with a stirrer, condensate take off, and nitrogen inlet head. The flask and contents were immersed into a Belmont metal bath and heated for two hours at 200–220° C. while ester interchange occurred. To carry out the polycondensation reaction, the temperature was increased to about 270° C. and the flask was held under vacuum at a pressure of about 0.5 mm Hg for about 20 minutes. The resulting polymer was dark blue and contained about 10% (w/w) blue colorant (yield - 174 g). The polymer was granulated by grinding in a Wiley mill. The procedure was repeated 5 times and all of the ground polymer was blended into one large sample. The composition sample had an I.V. of 0.31, a weight average molecular weight (Mw) of 20,085 and a number average molecular weight (Mn) of 9,121 by gel permeation chromatography (GPC) and a glass transition (Tg) at about 32° C.

EXAMPLE 9

A portion of the composite sample of Example 8 (600 g) was added to demineralized water (1500 mL) and the mixture stirred at near the boiling point until dispersion appeared complete. The final weight was about 2000 g, thus giving a 30% by weight dispersion of the polymeric colorant in water. The dispersion was filtered through a sintered glass funnel. Filtration was fast with no undispersed polymeric colorant observed. This colored dispersion was used to impart temporary coloration to human hair as described in U.S. Ser. No. 08/476,303.

TABLE I

Anthraquinone Compounds of Formula I

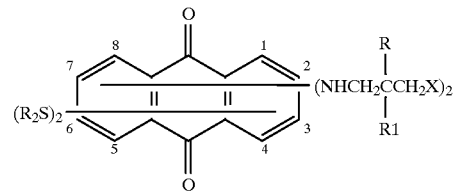

| Example | R, $R_1$ | Position of Amine Groups | $R_2$ | Position of Thio Groups | X |
| --- | --- | --- | --- | --- | --- |
| 10 | $diCH_3$ | 1,5 | $4\text{-}ClC_6H_4\text{---}$ | 4,8 | —OH |
| 11 | " | " | $4\text{-}BrC_6H_4\text{---}$ | 4,8 | $\text{---}OCOCH_3$ |
| 12 | " | " | $4\text{-}CH_3C_6H_4\text{---}$ | 4,8 | $\text{---}CO_2H$ |
| 13 | " | " | $3\text{-}CH_3CH_2C_6H_4\text{---}$ | 4,8 | $\text{---}OCOC_2H_5$ |
| 14 | " | " | $2\text{-}CH_3OC_6H_4\text{---}$ | 4,8 | $\text{---}OCON(CH_3)_2$ |
| 15 | " | " | $4\text{-}C_4H_9OC_6H_4\text{---}$ | 4,8 | $\text{---}CO_2H$ |
| 16 | " | " | $2,5\text{-}diClC_6H_3\text{---}$ | 4,8 | $\text{---}CO_2CH_3$ |
| 17 | $CH_2C_6H_5, CH_3$ | " | $3,4\text{-}diCH_3C_6H_3\text{---}$ | 4,8 | $\text{---}CO_2C_2H_5$ |
| 18 | $diC_6H_5$ | " | $2\text{-}Cl, 5\text{-}CH_3OC_6H_3\text{---}$ | 4,8 | —OH |
| 19 | $\text{---}CH_3, \text{---}CH_2CH(CH_3)_2$ | " | $4\text{-}C_6H_{11}C_6H_4\text{---}$ | 4,8 | —OH |
| 20 | diethyl | " | $4\text{-}C_6H_5C_6H_4\text{---}$ | 4,8 | $\text{---}OCO_2C_2H_5$ |
| 21 | $\text{---}CH_3, \text{---}CH_2CH_3$ | " | $4\text{-}CH_3C_6H_4\text{---}$ | 4,8 | —OH |
| 22 | $diCH_3$ | " | $C_6H_5\text{---}$ | 4,8 | —OH |
| 23 | $\text{---}CH_3, \text{---}CH_2C_6H_5$ | " | $C_6H_5\text{---}$ | 4,8 | —OH |
| 24 | $diCH_3$ | 1,8 | $C_6H_5\text{---}$ | 4,5 | —OH |
| 25 | " | " | $4\text{-}CH_3C_6H_4\text{---}$ | 4,5 | $\text{---}OCONHC_6H_5$ |
| 26 | " | " | $4\text{-}IC_6H_4\text{---}$ | 4,5 | $\text{---}OCONHC_6H_5$ |
| 27 | " | " | $4\text{-}CF_3C_6H_4\text{---}$ | 4,5 | —OH |
| 28 | " | " | $4\text{-}C_6H_5OC_6H_4\text{---}$ | 4,5 | —OH |
| 29 | " | " | $4\text{-}C_6H_5SC_6H_4\text{---}$ | 4,5 | —OH |
| 30 | " | " | $3\text{-}FC_6H_4\text{---}$ | 4,5 | —OH |
| 31 | " | " | $4\text{-}CH_3SO_2C_6H_4\text{---}$ | 4,5 | $\text{---}CO_2CH_3$ |
| 32 | —CH3, | " | $4\text{-}(CH_3)_2NSO_2C_4H_4\text{---}$ | 4,5 | $\text{---}CO_2CH_2CH_2OH$ |

TABLE I-continued

Anthraquinone Compounds of Formula I

| Example | R, R₁ | Position of Amine Groups | R₂ | Position of Thio Groups | X |
|---|---|---|---|---|---|
| 33 | —CH3,  | " | 1-Naphthyl- | 4,5 | —OH |
| 34 | C₆H₅, C₂H₅ 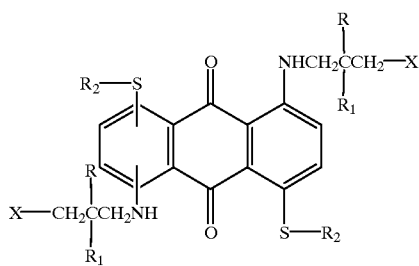 | " | 2-Naphthyl- | 4,5 | —OCOCH(CH₃)₂ |
| 35 | diCH₃ | 1,5 | 4-HOC₆H₄— | 4,8 | —OCOCH₃ |
| 36 | diCH₃ | 1,5 | 4(CH₃)₃CC₆H₄— | 4,8 | —OCOCH₃ |

We claim:

1. A compound comprising Formula I $$\text{I}$$

[Structure of Formula I shown with anthraquinone core bearing R₂—S groups, NHCH₂C(R)(R₁)CH₂—X groups]

wherein R and R₁ are the same or different and are selected from the group consisting of hydrogen and unsubstituted or substituted C₁–C₆ alkyl, C₃–C₇ cycloalkyl 2-furyl, 2-thienyl or phenyl; R₂ is aryl; X is a reactive group selected from the group consisting of hydroxy, C₁–C₆ alkanoyloxy, carboxy, C₁–C₆ carbalkoxy and carbamoyloxy.

2. The compound of claim 1 wherein R and R₁ are hydrogen and/or methyl; X is hydroxy or acetoxy; R₂ is selected from the group consisting of phenyl and phenyl substituted with methyl, ethyl, t-butyl, cyclohexyl, hydroxy, halogen, methoxy, ethoxy and mixtures thereof.

3. The compound of claim 2 wherein R and R₁ are both methyl.

4. The compound of claim 1 wherein R and R₁ are both methyl and R₂ is phenyl substituted with methyl.

5. Composition of matter comprising water-dispersible polymeric material having linking groups comprising at least about 20 mole % carbonyloxy and up to about 80 mole % carbonylamido, said material containing water-solubilizing sulfonate groups and having copolymerized onto or into the polymer backbone from about 0.01 to about 40 mole % based on the total of all reactant hydroxy, carboxy or amino equivalents, or the condensable derivative equivalents thereof, of colorant composition according to claim 1.

6. The composition of claim 5, wherein the polymer has an inherent viscosity of from about 0.1 to about 1.0 measured in a 60/40 parts by weight solution of phenol/tetrachloroethane at 25° C. and at a concentration of 0.25 gram of polymer in 100 mL of the solvent, the polymer containing substantially equimolar proportions of equivalents (100 mole percent) to hydroxy and amino equivalents (100 mole percent), the polymer comprising the reaction residues of the following reactants (a), (b), (c), (d), and (e) or the ester forming or esteramide forming derivatives thereof:

(a) at least one difunctional dicarboxylic acid;

(b) from about 4 to about 25 mole percent, based on a total of all acid, hydroxyl and amino equivalents being equal to 200 mole percent, of at least one difunctional sulfomonomer containing at least one cationic sulfonate group attached to an aromatic or cycloaliphatic nucleus wherein the functional groups are hydroxy, carboxyl or amino;

(c) at least one difunctional reactant selected from a glycol or a mixture of a glycol and diamine having two —NRH groups, the glycol containing two —CH₂—OH groups of which (1) at least about 10 mole percent, based on the total mole percent of hydroxy or hydroxy and amino equivalents, is a poly(ethylene glycol) having the structural formula:

$$\text{H(OCH}_2\text{—CH}_2\text{)}_n\text{ OH,}$$

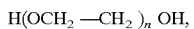

n being an integer of from 2 to 20, or (2) of which from about 0.1 to less than about 15 mole percent, based on the total mole percent of hydroxy or hydroxy and amino equivalents, is a poly(ethylene glycol) having the structural formula:

$H(OCH_2-CH_2)_n OH$, n being an integer of between 2 and 500, and with the proviso that the mole percent of said poly(ethlene glycol) within said range is inversely proportional to the quantity of n with said range;

(d) from none to at least one difunctional reactant selected from the group consisting of hydroxycarboxylic acids having one $-C(R)_2-OH$ group, a amino-carboxylic acid having one $-NRH$ group, and an amino-alcohol having one $-C(R)_2-OH$ group and one $-NRH$ group, or mixtures of said difunctional reactants; wherein each R in the (c) or (d) reactants is a H atom or an alkyl group of 1 to 4 carbon atoms; and (e) from about 0.1 mole % to about 15 mole %, based on a total of all acid, hydroxyl and amino equivalents being equal to 200 mole % of colorant composition according to claim 1.

7. The composition of claim 6 wherein the polymeric material contains less than about 10 mol %, based on all reactants, of reactant (d), at least about 70 mol % of reactant (c) is glycol, and at least about 70 mol % of all hydroxy equivalents is present in the glycol.

* * * * *